United States Patent [19]

Ginevri et al.

[11] Patent Number: 5,097,424
[45] Date of Patent: Mar. 17, 1992

[54] CONSTANT FLOW AND CONTROLLED VENTILATION, PRESSURE RESPONSIVE PULMOTOR

[75] Inventors: Giorgio Ginevri; Corrado Moretti, both of Rome, Italy

[73] Assignee: Elmed Genevri Srl, Rome, Italy

[21] Appl. No.: 672,000

[22] Filed: Mar. 18, 1991

Related U.S. Application Data

[63] Continuation of Ser. No. 135,443, Dec. 18, 1987, abandoned.

[30] Foreign Application Priority Data

Dec. 31, 1986 [IT] Italy ................. 48798 A/86

[51] Int. Cl.⁵ .................... G06F 15/42; A62B 7/00
[52] U.S. Cl. .................... 364/510; 128/204.23; 364/413.03
[58] Field of Search ............ 364/413.01, 413.02, 364/413.03, 510, 550; 128/204.11, 204.14, 204.17, 204.23, 204.24, 204.25, 204.26, 716

[56] References Cited

U.S. PATENT DOCUMENTS

| | | | |
|---|---|---|---|
| 4,305,388 | 12/1981 | Brisson | 128/204.17 |
| 4,417,573 | 11/1983 | DeVries | 128/204.25 |
| 4,425,805 | 1/1984 | Ogura et al. | 364/510 |
| 4,462,398 | 7/1984 | Durkan et al. | 128/204.23 |
| 4,565,194 | 1/1986 | Weerda et al. | 128/204.23 |
| 4,589,409 | 5/1986 | Chatburn et al. | 128/204.25 |
| 4,617,637 | 10/1986 | Chu et al. | 364/510 |
| 4,635,631 | 1/1987 | Izumi | 128/204.23 |
| 4,671,297 | 6/1987 | Schulze, Jr. | 128/204.23 |
| 4,682,591 | 7/1987 | Jones | 128/204.25 |

*Primary Examiner*—Kevin J. Teska
*Attorney, Agent, or Firm*—Mason, Fenwick & Lawrence

[57] ABSTRACT

A constant flow and controlled-ventilation pulmotor responsive to the respiration pressure in the respiratory circuit of a patient in which the intervention of a processor causes visually observable information to be presented to the operator to allow immediate control of mechanical ventilation and the adaptation of same to the clinical requirements of the patient. First, second and third desired pressure, time and flow rate parameters are set by a control board. A maximum pressure-responsive valve is responsive to the first pressure, time, and flow rate parameters, a minimum pressure-responsive valve is responsive to the second pressure, time, and flow rate parameters, and a solenoid valve is responsive to third pressure, time, and flow rate parameters. A transducer continuously detects in real time the value of the instantaneous pressure in the respiratory circuit of the patent and supplies an electrical signal indicative thereof to the processor. The processor processes the signals from the transducer and the control board and respectively visualizes them on a video display as breathing waveforms and as numerals representative of the first, second, and third sets of parameters.

2 Claims, 8 Drawing Sheets

CONSTANT FLOW AND CONTROLLED VENTILATION, PRESSURE RESPONSIVE PULMOTOR

This application is a continuation of U.S. patent application Ser. No. 07/135,443, filed Dec. 18, 1987, now abandoned.

BACKGROUND OF THE INVENTION

The present invention relates to a constant flow and controlled ventilation, pressure responsive pulmotor. More particularly, the present invention relates to a pressure responsive pulmotor of the type mentioned above wherein means are provided for a control action intended for keying and detecting the behavior of the ventilation operation and possibly for modifying the same in real time according to the current needs. Pressure responsive pulmotors employed at present make use of mechanical devices, such as for instance of aneroid pressure gages for controlling and reading pressure values, so supplying only incomplete and approximate information about what is occurring within the circuit in which the patient is inserted.

In addition, the drawback of the manual recording of information data which requires quite long working times and implies the possibility of information loss adds to such uncontrolled running of the leaving parameters for carrying out correctly the ventilation operation.

It is clearly evident that there is the need for a constant flow pressure responsive pulmotor in which the intervention of the processing means causes visually observable information to be presented to the operator so as to allow an immediate control to be performed of mechanical ventilation, adapting the same to the clinical requirements and eliminating thus the drawbacks mentioned above which are due to the manual control of mechanical, pressure responsive ventilation machines known up to the present time.

In practice, and this normally occurs in the control system of the present invention, one or more parameters are keyed which can be defined as the keyed parameters and are characteristic of the operation and which are of such values as to exert on the operation itself the desired controlling action. More specifically, they are:

inhalation time Ti
exspiration time Te
peak pressure PIP
final inhalation pressure PEEP
pressure increase rate (flow in 1/minute).

Such keyed parameters correspond to those which are to be subjected to the desired behavior, and specifically:

the inhalation rate (Rate)
the inhalation/expiration ratio I/E
the waveform (triangular wave, square wave)
the pressure gradient between PIP and PEEP
the mean inhalation pressure MIP
the mean pressure over a whole respiratory cycle
  MAP which parameters allow the operator to estimate clinically the behavior of the therapeutical treatment as each one of them has a well definite clinical meaning.

SUMMARY OF THE INVENTION

Accordingly, the optimization of the control function proposed by the present invention during the artificial breathing by pulmotor means to offer to the operator the immediate visual perception even at a distance of some meters of the whole behavior of the base parameter, i.e. of the pressure applied to the respiratory apparatus of the patient.

In order to correctly estimate the importance of the controlled parameters mentioned above in performing a suitable ventilation for the patient, it is opportune to recall even as a brief overview, their specific meaning.

The peak inhalation pressure (PIP) level is the main parameter in determining the volume of the fluid (air-+oxygen) administered to the patient. In case of respiratory insufficiency due to extrapulmonar causes (apnoea crisis, drug depressions and so on) a low PIP will be enough for assuring a suitable volume; in case of respiratory insufficiency consequent to a pulmonary disease with reduced compliance (RDS, bronchopneumonia, pulmonary oedema) a higher PIP value will be required.

Pressures of insufficient values will prevent a good oxygenation and a suitable removal of $CO_2$ from occurring; pressures of excessive values can be the cause of interstitial emphysema, pulmonary breaking pneumomediastinum, pneumothorax, and can prevent the venous return from occurring (arterial hypotension).

The selection of the PIP level to be employed can tentatively be based on the percentage concentration of oxygen in the air necessarily inhaled by the patient; i.e., the air the oxygen demand, the air the PIP level to be employed which can be obtained from the ventilation tables; the clinical estimate of thorax expansion is also an important parameter.

In new-born babies, breathing rates are commonly employed between 40 and 60 breathing acts/minute; air rates (up to 120 acts/minute) can be of benefit in some particular clinical conditions such as the persistency of foetal circulation or of diaphragm hernia.

In the absence of severe pulmonary diseases, the optimal Ti value is of about 0.4–0.5 sec; in case of remarkable reduction of the pulmonary compliance with the need for high percentage concentrations of oxygen in the inhaled air, the value of Ti can be increased up to 0.7–0.8 sec for improving oxygenation.

When the clinical conditions are better, the Ti value is to be again reduced.

Once the optimal values of Ti and PIP have been keyed, the value of Te is to be adjusted so as to assure a respiratory rate which keeps the partial pressure of $CO_2$ in artery blood between 30 and 40 mm Hg; the usual values change between 0.5 and 1 sec so as to obtain a breathing rate between 30 and 40 breathing acts/minute. When long Ti values or high breathing rates are employed, the Te value is to be reduced; too short a Te value may however be insufficient in allowing a complete expiration with the consequent trapping of gases within the circuit and the breathing apparatus.

The value of the I/E ratio depends on the value of the Ti keyed by the operator for obtaining an optimal oxygenation as well as on the Te value for allowing a suitable elimination of $CO_2$; accordingly such ratio is always a derived parameter which is never set forth in advance.

The flowrates normally employed are variable between 2 and 10 l/minute; the flowrate also determins the pressure waveform.

A low flowrate gives rise to a triangular-type wave which is more physiological and less traumatic: the pressure rises slowly up to the desired level almost at the end of the Ti time. A high flowrate gives rise to a square-type waveform: the pressure rapidly reaches up to the desired level and keeps such value for the whole duration of Ti (the plateau or inhalation pause).

The length of the plateau at a given Ti can thus be varied by increasing or decreasing the flowrate.

In the approaching phase it is always advisable to use a triangular waveform; in case of remarkable reduction of the pulmonary compliance with a strong need for a percentage concentration of oxygen in the air inhaled, it will be necessary to have recourse to a square waveform for better oxygenation.

The employment of too high flowrates causes the risk of pulmonary breaking; on the contrary, too low a flowrate may not be enough for reaching the pressure level desired.

The mean pressure at the level of the breathing apparatus (MAP) points out the average value of pressure at the level of the breathing apparatus during a whole breathing cycle, and expresses the integration of all parameters intervening in its formation: PIP, Ti, Te, the pressure waveform and PEEP; its value can be calculated by solving the following equation:

$$MAP = K(PIP - PEEP) \cdot Ti/(Ti + Te) + PEEP$$

where K is a constant depending on the pressure increase rate; if the wave is of the square type, the value of K is close to 1 whereas if the wave is triangular the value of K is of about 0.5.

The value of the MAP can also be increased by increasing the inhalation flowrate so as to obtain a square wave; or by increasing the level of PIP; or by increasing the value of Ti; or by increasing the PEEP value.

The mean inhalation pressure (MIP) points out the average value of pressure at the breathing apparatus level during an inhalation act; as Te is excluded, its value is certainly more efficient than that of MAP in expressing by a single datum the integration of the parameters which determin the kind of wave employed and accordingly it is of higher usefulness as a leading or guiding parameter for running the ventilation operation. Its value can be calculated by solving the equation:

$$MIP = K(PIP).$$

The positive expiration end pressure (PEEP) acts by increasing the residual functional capability and hence:
it avoids the alveolar collapse
it exerts a protective action on the surfactant
it decreases the resistance of the breathing apparatus Thus, it determines the improvement of the alveolar ventilation and of the ratio between the ventilation and the perfusion.

In order to satisfy such requirement, the present invention suggests the employment of a constant flow pressure responsive pulmotor as a single unit provided with a control electronic system for the processing of the keyed parameters into controlled parameters which can be visualized during the whole operation of the ventilation apparatus, on a monitoring screen which is connected to a printing unit.

According to the present invention and on the basis of the preceding considerations, a constant flow pressure responsive pulmotor is suggested which is characterized in that it comprises in a single unit mixing means for the proportioning of the amounts of air and oxygen, means for the regulation of the flow fed to the inhalation conduit in which some valve means are provided for intercepting the flow in correspondence to a maximum value set forth previously of the inhalation pressure ($V_{MAX}$) and humidifying and heating means controlled by a servo system, solenoid valve means inserted in the expiration conduit, such conduit being provided at its discharge end with valve means for discharging the air breathed out in correspondence to a minimum pressure value ($V_{MIN}$), an electronic processor unit for converting the keyed parameters into controlled parameters, keyboard means for keying said keyed parameters, monitoring means for visualizing said controlled parameters and printing unit means for the transcription of said controlled parameters, as said electronic processor unit is provided with an information file for keying and running correctly the ventilation operations.

According to a preferred embodiment of the present invention, the control board of said electronic processor unit comprises calibrated knob means for the regulation of the oxygen concentration in the mixture and for the regulation of the air-oxygen mixture flowrate; push button means for keying the values of the inhalation and expiration pressures which are intended for the adjustment of said valves $V_{MAX}$ and $V_{MIN}$, knob means for keying the inhalation and expiration times, and knob means for keying the alarm values respectively for the maximum and the minimum values of pressure; key means for the activation and disactivation of the video image and of the printing unit.

Said knob means are prearranged for keying said oxygen percentage at values from 21 to 100% and the flowrate of the feed mixture from 0 to 20 l/minute. Some sound alarm means are also provided which become active when the pressure level between the two circuits coming from the air source and from the oxygen source exceeds the value of 1 atmosphere.

It is also to keep in mind that the maximum service pressure that can be sustained by the mixer flowmeter is of 6 atmospheres (the best service pressure is of 3.5 atmospheres).

According to a preferred embodiment, the monitor screen is provided in its upper portion with a subdivision into small boxes in which the values of the following parameters are visualized:
the breathing rate (Rate)
the inhalation time Ti
the expiration time Te
the ratio I/E
the level of $P_{MAX}$ (PIP)
the mean inhalation pressure value and the mean pressure in the whole respiratory cycle MIP-MAP
the pressure level at the end of the expiration PEEP
the ventilation time stored and in its lower portion, with a space for the visual presentation, on a pressure-time plot, of the pressure waveform as a function of the time between the successive inhalation (PIP) and expiration (PEEP) phases, said pressure waves pointing out in real time the value of the mean pressure in the respiratory apparatus during a whole respiratory cycle (MAP) as well as the mean value of pressures during the inhalation cycle only (MIP).

Pressure waves go into the video (of the monitor) from left to right, so eliminating the preceding image. The construction of such plot occurs in real time by means of the continuous detection of the instantaneous pressure in the patient's circuit and its transduction into an electric signal. Such signal is of the analog type as it varies continuously in time. Such signal in addition is to be converted into a sequence of binary digits at the rate of one pulse per 30 ms for its employment in the operative unit.

The particular meaning of the MAP can be observed as the controlled parameter which is representative of all keyed parameters intervening in the keying operations of the respiratory cycle. Indeed, said MAP is the value of the average pressure at which the respiratory apparatus is exposed during a whole cycle and, as already mentioned above, it can be calculated by solving the following equation $$MAP = K(PIP - PEEP) \cdot Ti/(Ti + Te) + PEEP$$

wherein K is a constant that depends on the pressure increase rate. Accordingly, said MAP can be controlled through keying:
1) the pressure increase rate
2) PIP
3) Ti
4) PEEP
5) Te.

The value of the MAP is correlated to the patient's oxygenation degree. However, there is the possibility that the operation of controlling such value is in contrast to the elimination of $CO_2$: the PEEP increase improves the oxygenation as it increases the value of the MAP, but it lowers the volume flow as it lowers the pressure gradient.

Accordingly, the assumption of oxygen at alveolar level depends on MIP in a more direct and autonomous way, said MIP being the mean value of pressure during inhalation.

The control of the MIP is thus effected by the parameters with which the inhalation phase is keyed: the pressure increase rate, the value of Ti and the value of PIP. It follows from the above that, in the general balance of mechanical ventilation, a good running of the inhalation phase is based on the search for of the MIP value that is suitable to give a sure optimal oxygenation and at the same time to cause the least possible damage.

The graphical expression of the MIP as the measure of the area under the inhalation pressure curve is an information which is abundant in shades of meaning. Indeed, the control of the inhalation measure offers the advantage of visualizing a formal characteristic of the MIP: the shape of the wave is usually controlled on the basis of the pulmonary disease type.

It is well evident that such control allows the estimate to be carried out of all changes in the measure of the areas under the pressure wave curve so giving the operator an accurate information about the value of said MIP and obviously, by inclusion of the Te, also of the MAP.

As can be deducted, the distance between the PIP and the PEEP is proportional to the volume of the gas that is made to flow up to the patient in unit time. The image of such distance as appears on the video of the control system of the present invention is integrated with the image of the distance that separates an inhalation peak from the other one.

Accordingly, the first one of two such intervals in the plane (which is the representation of the $\Delta p$ as the ordinates) gives an idea of the volume flow whereas the second one (that is the representation of Te as the abscissas) gives the operator the visual perception of the breathing rate (see also FIGS. 7-8).

The breathing rate together with the volume flow contributes to form the volume minute of which the $CO_2$ eliminated is a function.

Thus the Te shows the parameter to be keyed in order to obtain, through the control of the breathing rate, the $CO_2$ desired. The ratio I/E accordingly is not an application previously set forth of a treatment scheme but it is simply a derived value resulting from a mental process of deductive type in which the problem of respiratory insufficiency is tackled in a selective way through the independent running of the two phases of the artificial respiratory cycle.

According to a preferred embodiment of the pressure responsive pulmotor of the present invention, said solenoid valve means are made up of a pinchcock solenoid valve which can be rapidly substituted and exerts its action on the outer surface of the conduit of the expiration air. The pulmotor according to the present invention is also advantageously endowed with a spare solenoid valve which can be employed in case of fault.

Again advantageously, a bottle can be provided in the conduit of the expired air downstream the valve $V_{MIN}$ for the collection of the condensate.

Advantageously, key control means are provided on the control board for the variation of the representation scale of the pressure waveform on the video.

Moreover, the electronic processing unit contains a file of information data regarding the operations for the preparation of the patient to ventilation, as well as the operations of intubation and connection to the pulmotor and of prescription of intervention during the working cycle.

The pulmotor is previously arranged in a suitable way for connection to a heart rate meter for automatic intervention in case of bradycardia.

BRIEF DESCRIPTION OF THE DRAWINGS

The present invention will be disclosed in the following just for illustrative and not for limitative purposes with reference to the enclosed drawings wherein.

DESCRIPTION OF THE PREFERRED EMBODIMENT

Figure 1:
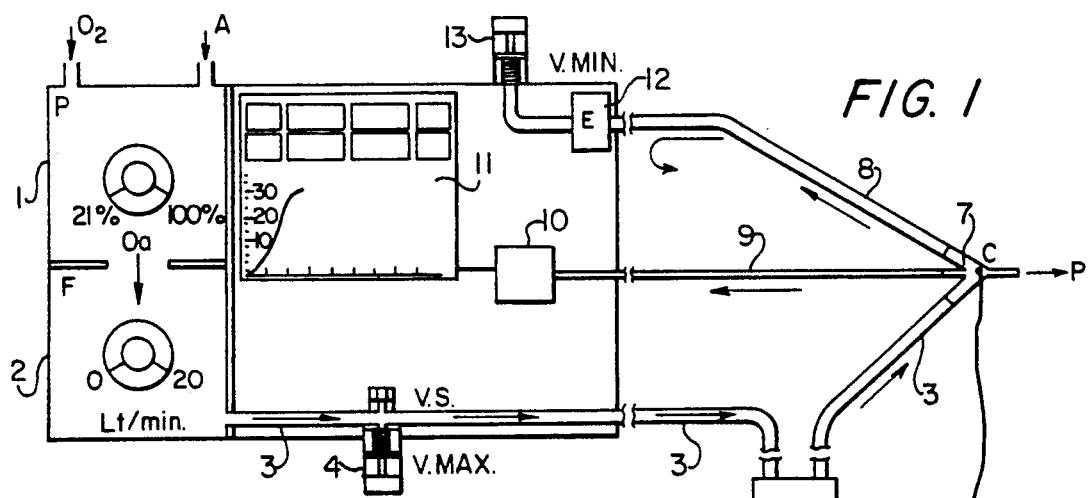
FIG. 1 is a schematic view of the pulmotor of the present invention in which the pinchcock solenoid valve is closed so as to deviate gas flow to the patient.
Figure 2:
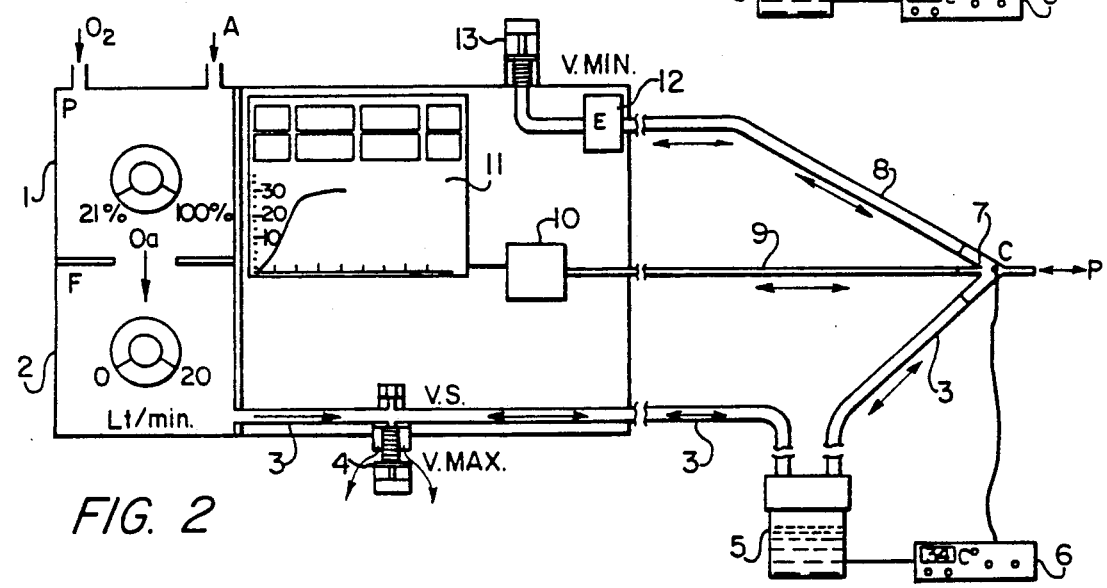
FIG. 2 is a schematic view of the pulmotor of FIG. 1, in which the inhalation pressure (PIP) has reached the desired level inside the circuit.
Figure 3:
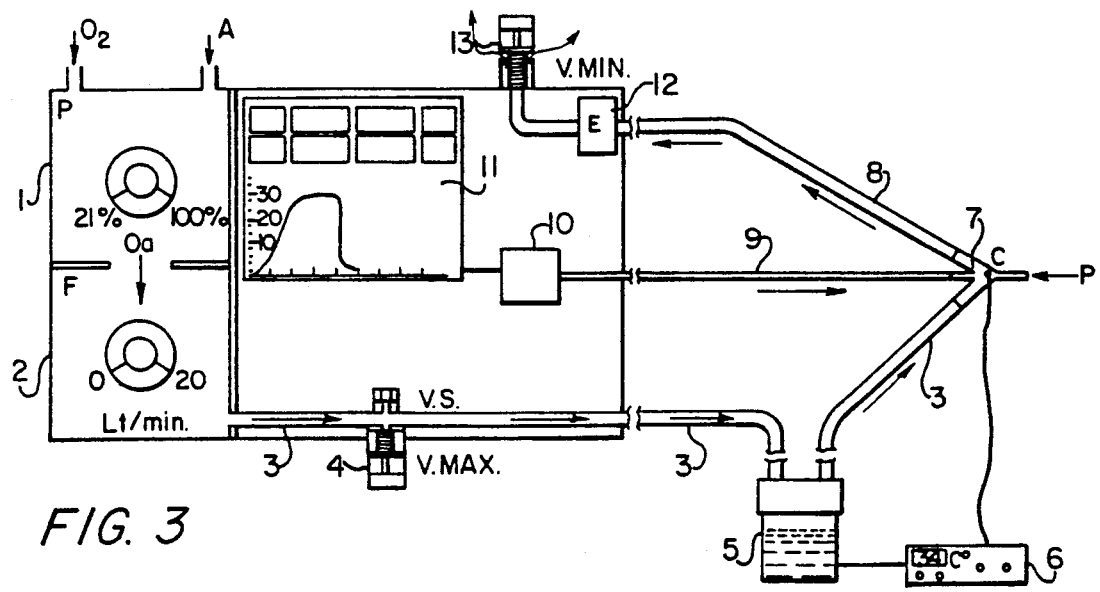
FIG. 3 is a schematic view of the pulmotor of FIG. 1, in which the minimum pressure responsive valve is opened for discharging the inhaled air.

With particular reference to FIGS. 1, 2 and 3, the feeding lines can be observed of oxygen and air, respectively $O_2$ and A, to the proportioning unit 1 wherein the percentage oxygen in the feed mixture is determined within a range between 21 and 100%. The mixture ($O_2$ and A) so obtained passes from that unit to the flowmeter 2 wherein the feed flow to the inhalation conduit 3 can be adjusted within a range of values between 0 and 20 l/minute.

A valve 4 (VMAX) limiting the value of the inhalation pressure (PIP) is provided in said conduit 3, such valve intervening in correspondence to a maximum value set forth previously for the inhalation pressure.

The humidifier-heater 5 is provided along said conduit 3 downstream to valve 4, said humidifier-heater being controlled by the servo system 6. The conduit 3 is connected to the patient P who has been intubated previously through the three-ways connection unit 7. The conduit 8 for the expiration air and the conduit 9 which is connected through a transducing unit 10 to said electronic processor unit 11 which is provided with a monitor, are both connected to said connector 7.

A pinchcock solenoid valve 12 is provided along said conduit 8, said solenoid valve operating on the outer surface of said conduit so as to warrant optimal boundaries to the sterility conditions. The conduit 8 has at one of its ends the valve 13 ($V_{MIN}$) intervening for opening said conduit and for discharging the inhaled air till the expiration pressure (PEEP) reaches the minimum pre-established value (FIG. 3).

As a matter of practice, the flowmeter 2 dispenses a constant flow of air and oxygen which flow through the ventilation circuit 3; the valve 12 closes intermittently and for a predetermined time Ti the expiration way so as to deviate the gas flow to the patient (FIG. 1). As already mentioned above, the basic parameter for the ventilation of the patient is the insufflation pressure (PIP); when such pressure reaches the desired level inside the circuit, any excess of gas that is possibly present is eliminated into the environment by the valve 4 ($V_{MAX}$) that limits the value of maximum pressure, and is arranged along the inhalation way 3. This fact allows the fine adjustment to be obtained of the maximum inhalation pressure and also allows such pressure level to be kept during the whole further inhalation time (FIG. 2).

The valve 13 ($V_{MIN}$) is arranged, as already mentioned above, at the end of the expiration circuit, said valve offering an adjustable resistance to the outflow of gas in correspondence to the opening and closing of the expiration conduit controlled by said solenoid valve 12, thus allowing the end expiration pressure to be finely adjusted (FIG. 3). The transducer continuously detects the instantaneous pressure in the ventilation circuit so supplying the signal to the control electronic system which also provides the processing of data and their visualization on the video 11.

Figure 4:
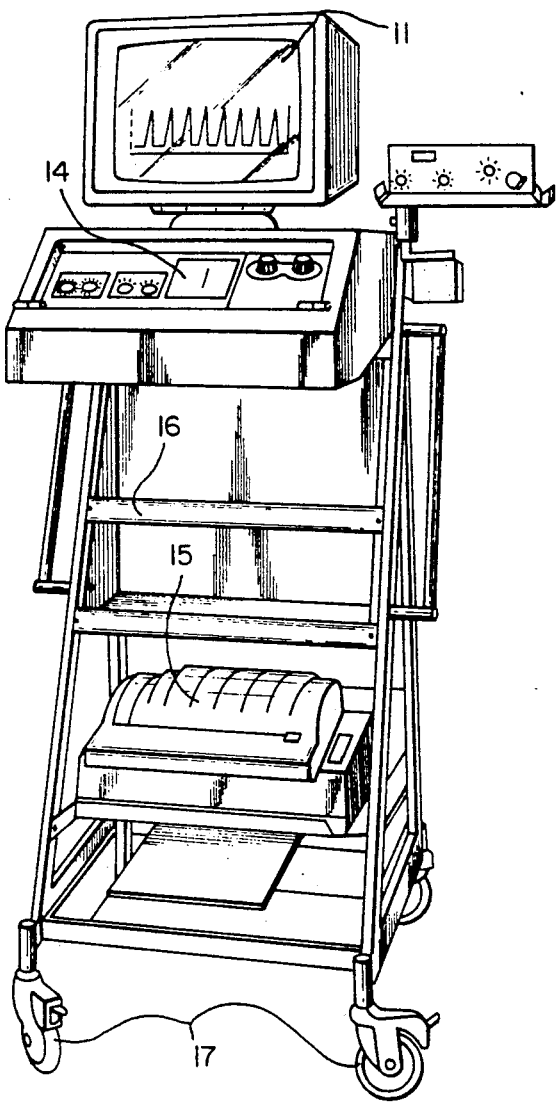
FIG. 4 is a front perspective view of the pulmotor of the present invention.
Figure 5:
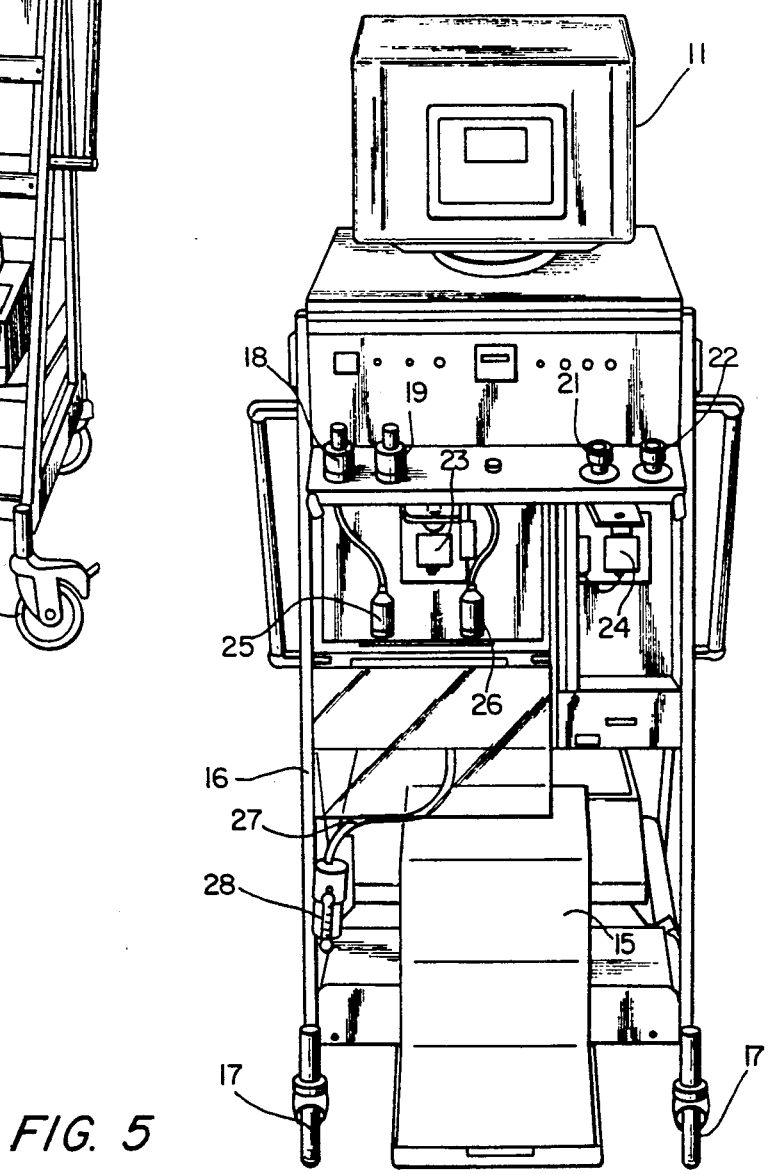
FIG. 5 is a rear plan view of the pulmotor as shown in FIG. 4.

A clear vision of the outer structure of the unitary system consisting of the pulmotor with electronic control of the image can be obtained by observing FIGS. 4 and 5.

With a detailed observation starting from the top and proceeding downwards, the presence can be remarked of the monitoring screen 11 which is connected to an electronic processing unit (not shown), of the control board 14 of the work operations (which is shown in a more detailed way in FIG. 6), of the printing unit 15 collected into a single structure resting on the frame 16 running on the wheels 17. The rear view (FIG. 5) shows in addition as essential members the outlet 18 for feeding the gas mixture to the patient and the return 19 of the expiration gas from the patient, the connection 20 for the pressure detecting pipe, the rapid-type connections 21 and 22 respectively for oxygen and air and the pinchcock solenoid valve 23 which operates on the expiration conduit 8 and an identical spare solenoid valve 24 housed in a suitable groove, the valves $V_{MAX}$ and $V_{MIN}$ which are pointed out by the numerals 25 and 26, the connection conduit 27 for the discharge which is endowed with the bottle 28 for the collection of the condensate.

Figure 6:
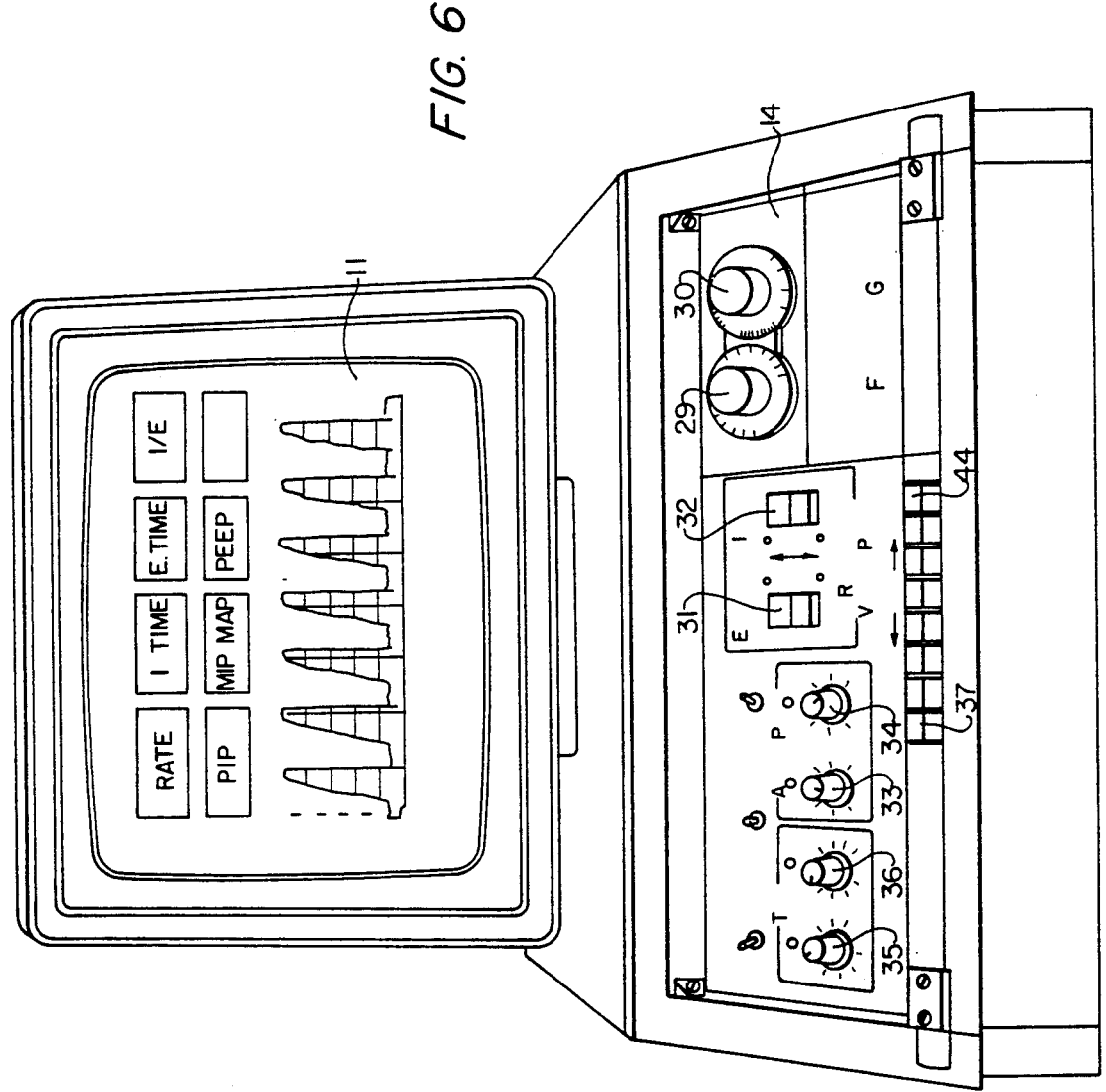
FIG. 6 is a front plan view of the monitor and control board of the pulmotor shown in FIG. 4.

FIG. 6 shows in its essential details the monitoring group with the screen 11 and the control board 14. On said control board 14, the presence can be observed from right to left first of all of the knobs for the regulation of the concentration of $O_2$ and of air in the feed mixture and respectively for the regulation of the flowrate of the $O_2$ and air mixture to the pulmotor, which knobs are pointed out by the numerals 29 and 30 and operate on calibrated housings in the range from 21 to 100% as for the oxygen percentage and from 0 to 20 l/minute as regards the feed flowrate of the mixture.

Next the key control means 31 and 32 are provided for keying the keyed parameters consisting respectively of the inhalation and the expiration pressure, then the knobs 33 and 34 are provided for keying the minimum and maximum pressure values beyond which an alarm system intervenes and then the knobs 35 and 36 for keying respectively the times Ti and Te.

A series of keys 37–44 in the central zone allows, in a succession from the left to the right the operations of "freezing" and of "thawing" of the video image to be performed, as well as the operations of changing the scale of representation, of turning the page of the file kit of the processor unit, of printing and of the timer.

The screen 11 shows on the contrary an upper space bearing eight small boxes divided into two overlapping lines for the visualization of the following parameters: rate, Ti, Te, I/E, PIP, MIP-MAP, PEEP, and the ventilation time during employment of the pulmotor.

In the lower part, the space is allowed on a diagram with pressures expressed as cm $H_2O$ on the ordinates and times in seconds as the abscissas, for the visualization of the pressure waves that show objectively in real time the values of the MIP and MAP which are essential for controlling immediately the behavior of the ventilations when the working conditions are changed.

Figure 7:
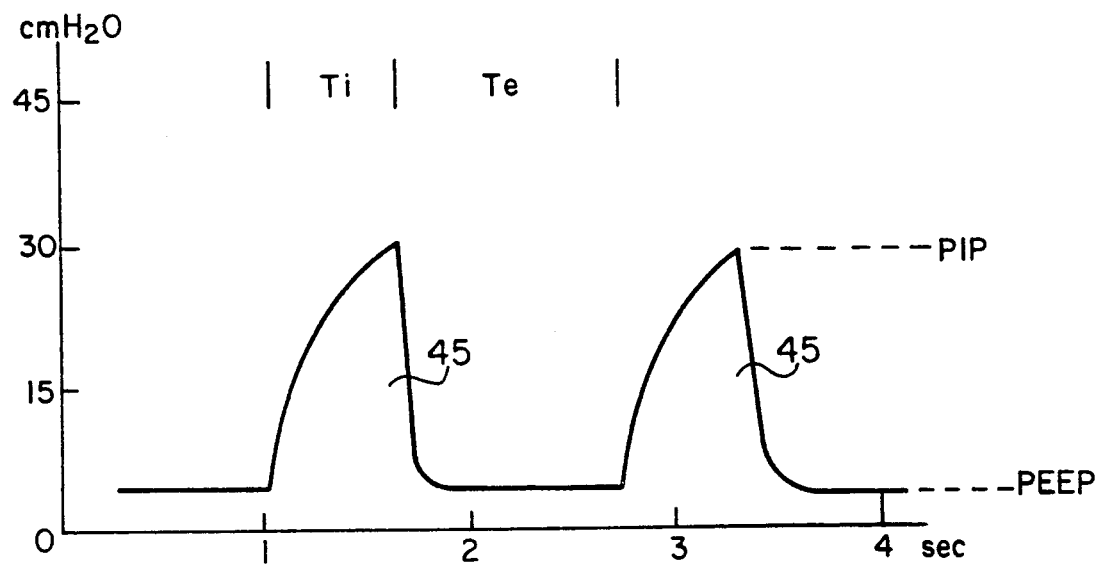
FIG. 7 is a graphic representation of a pressure waveform which appears in real time on the monitor shown in FIG. 6, as a result of the continuous detection of the instantaneous pressure in the patient's circuit and the transduction of such pressure into an electrical signal as a function of TeTi values and of PIP and PEEP values by the pulmotor of the invention.
Figure 8:
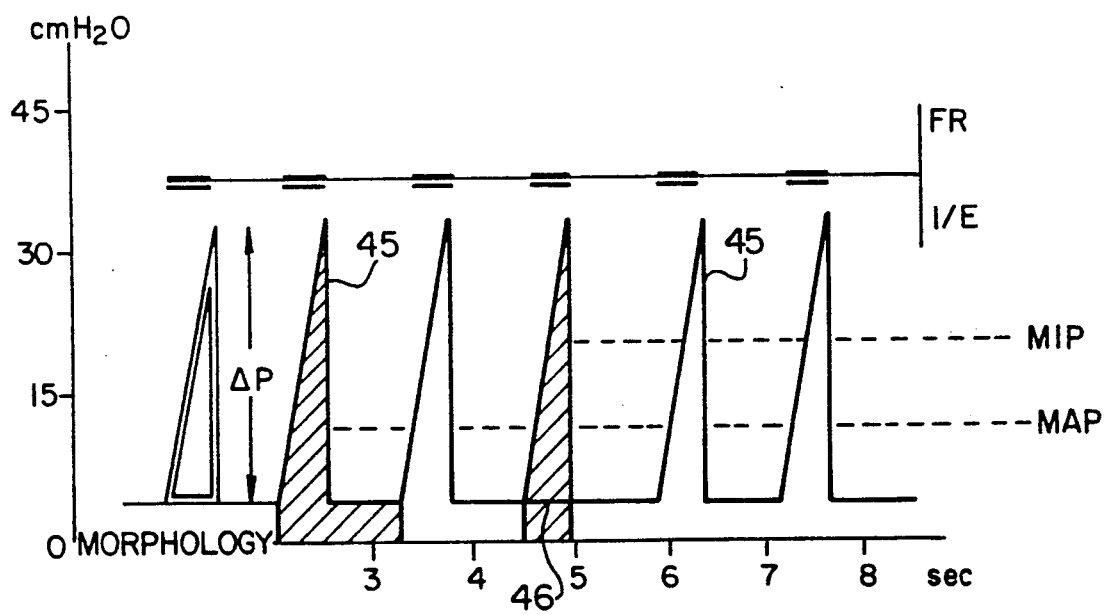
FIG. 8 is a graphic representation displaying in an alternate manner the pressure waveform of FIG. 7.

In the next FIGS. 7 and 8 the representations are shown on an enlarged scale of various pressure waves, more particularly FIG. 7 shows the pressure waveform 45 which appears in real time as a result of the continuous detection of the instantaneous pressure in the patient's circuit and the transduction of such pressure into an electrical signal as a function of Te and Ti values as well as of PIP and PEEP values all previously set forth.

FIG. 8 shows in a better way the meaning of the pressure waves 45 which allow, as already mentioned above, the values of MIP and MAP to be estimated for a previously established difference between PIP and PEEP and the respiratory rate FR. The dotted zone 46 shows with its total area the value of MAP+MIP, the value of MIP being given by the rectangular area between the axis of the abscissas and the parallel line corresponding to the PEEP value during the inhalation act.

The present invention will be disclosed in the following example in its application to a particular clinical case of the hyaline membranes disease so as to make it clear the understanding of the characteristics of efficiency and reliability of the apparatus of the invention itself.

A baby, the first of a pair of twins, the son of T.C. E.G., 35 weeks; weight kg 2 (25° centile); Apgar 7-9.

About one hour after birth the new-born baby begins to show dispnoea and cyanosis crisis; the baby is hospitalized in the new-born department where the baby arrives, aged six hours in very serious general conditions; the clinical symptoms characterize a severe respiratory insufficiency. The baby is intubated and connected to the M.O.G./2000 pulmotor working on the following parameters:

| | |
|---|---|
| Ti = 0,4 sec | FiO$_2$ = 1 |
| Te = 0,6 sec | PIP = 20 cmH$_2$O |
| FR = 60/min | PEEP = 3-4 cmH$_2$O |

The radiological diagnosis confirms the suspicion of MIP.

After improvement of short duration of the clinical conditions, such conditions begin to get worse and a PaO$_2$ higher than 50 mmHg cannot be obtained even with a PIP increase from 20 to 28 cmH$_2$O to increase the volume flow; moreover, the baby looks very restless and clearly wrestling with the pulmotor.

When the baby is aged 15 hours the decision is made of treating the patient with curare to warrant a good adaptation to the pulmotor and to modify the parameters of latter in an attempt at improving ventilation.

In the following disclosure reference is made to the further FIGS. 9-16 wherein the pressures on the ordinates are reported as cmH$_2$O and times in seconds are reported as the abscissas.

Figures 9, 10:
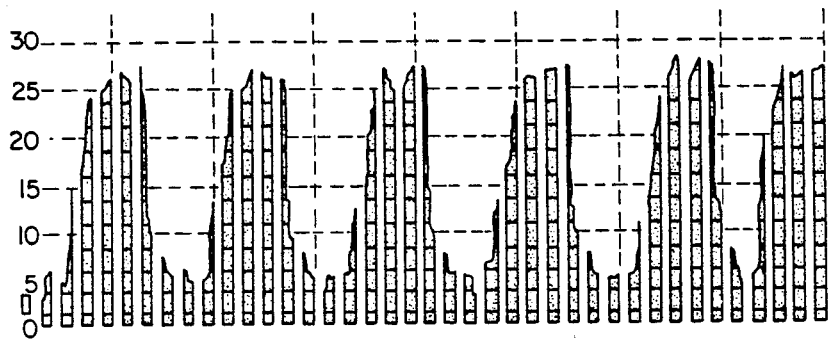
FIG. 9 shows a real time print out of the parameters of the pulmotor of the invention and of the pressure waveform detected in the ventilation circuit shortly after the treatment of a patient with curare and a change of parameters.
FIG. 10 shows the MIP that is determined by the integration of the three parameters involved in the formation of the pressure wave.

FIG. 9 shows the print out obtained in real time of the parameters of the pulmotor and of the pressure waveform detected in the ventilation circuit shortly after the treatment of the baby with curare and the change of parameters.

The following considerations can be obtained from the analysis of such Figure:

1) the value of Ti has been increased from 0.4 to 0.8 seconds; on the contrary the value of Te is kept unchanged; thus the ratio I/E is inverted.

The employment of a long Ti is made optimal by the treatment with curare and it allows the realization to be obtained of a pressure wave of the square type, i.e. the pressure increase rate (stemming from the value of the flowrate) is of such a value as to allow the desired PIP of 28 cm H$_2$O to be rapidly reached and then to be kept for the remaining part of Ti (the plateau or inhalation pause).

The small pressure oscillations detectable above all during the inhalation pause can be referred to the presence of the condensate in the circuit.

2) The value which is best correlated singly with the oxygenation degree, above all in the hyaline membranes disease is the MIP that is determined by the integration of the three parameters involved in the formation of the pressure wave, i.e. Ti, flowrate (or flowrate from which the waveform stems) and PIP (that determines the value of Vt (FIG. 10).

The increase in Ti and the inhalation pause (the square waveform) with an increase in the MIP, cause the oxygenation to be improved, first of all because in that way the diffusion of O$_2$ at the alveolar level as well as a more uniform distribution of the gas among zones having different compliances (a compliance difference implies different times of alveolar filling, i.e., both "rapid" and "slow" alveoli exist) are both favored; thus the formation of atelectasias is contrasted, with a consequent improvement of the V/Q ratio. On the contrary, the use of a rapid Ti with triangular waveforms can cause the ventilation mainly of the alveoli which ar already expanded and the increase of PIP beyond the limit which is necessary to assure a good expansion, causes the risk of hyperdistension and breaking. Finally it is to be remarked that the increment of PIP in a waveform of such a type will cause a low increase in MIP, to the contrary of what occurs with a square-type wave and with a long Ti.

3) The analysis of gas (FIG. 9) which was carried out shortly after such changes, shows a good vetilation; the value of the FR is sufficient to warrant an adequate elimination of CO$_2$ and then any change in Te is useless.

In the next ten hours (FIG. 11) it was possible to decrease gradually the value of FiO$_2$ down to the value of 0.6; the other parameters were left unchanged except for the value of PIP that was lowered to 25 cmH$_2$O.

The decrease in the O$_2$ percentage to warrant a good oxygenation is an index of gradual improvement in the pulmonary pathology, which is to be followed by a similarly gradual decrease in the insufflation pressures employed (PIP and MIP).

Figure 11:
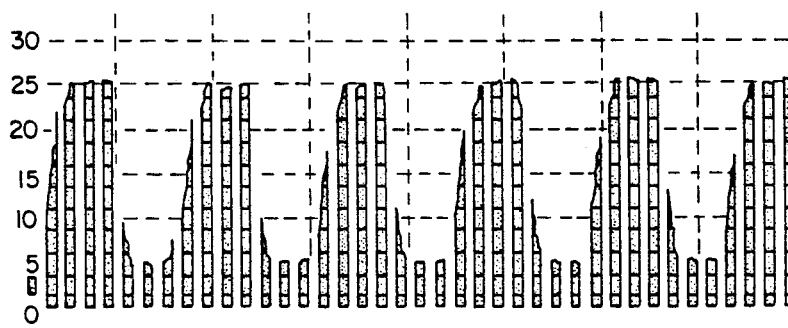
FIG. 11 shows the real time print out of the parameters of the pulmotor of the invention and of the pressure waveform detected in the ventilation circuit with the value of $FiO_2$ decreased down to a value of 0.6 and the other parameters remaining constant from FIG. 9.

It is to be remarked in FIG. 11 that the absence of condensate water from ventilation circuit (or of secretions from the tracheal cannula) allows a graphic image to be obtained which is free from oscillations. The clinical conditions of the baby continue to improve and when the baby is aged 40 hours the $FiO_2$ has decreased down to 0.4 (FIG. 12).

Figure 12:
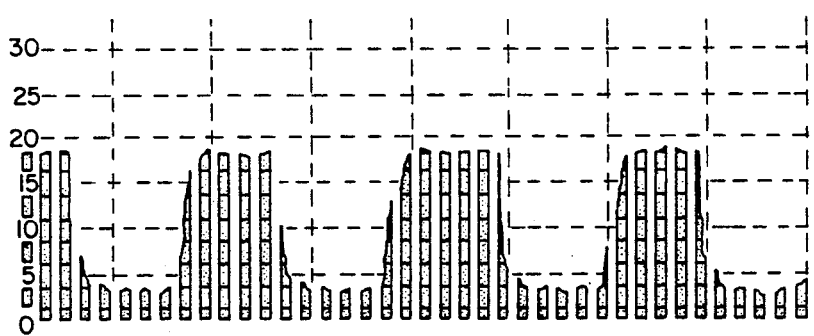
FIG. 12 shows the real time print out of the parameters of the pulmotor of the invention and of the pressure waveform detected in the ventilation circuit with the value of $FiO_2$ decreased down to 0.4 from that of FIG. 11.

From the analysis of FIG. 12 the following comments can be made:

1) the PIP reduction from 25 to 18 $cmH_2O$ is correct, the need being considered for a less percentage of the $O_2$ inhaled;

2) the Ti value is too long; the operator in order to key a I/E ratio of 1/1, i.e. in order to make such Ti more physiological and in order to decrease simultaneously the value of the FR in order to make the $PaCO_2$ to increase and then to start the removal of curare, has keyed a Ti/Te of 1 sec/1 sec. While this philosophy is correct for Te, it is definitely uncorrect as regards Ti. Indeed, the correct procedure would have been that of reducing Ti with respect to the value previously employed (0.8 sec) and to modify the waveform so as to make the same more triangular (a lower flowrate so that the PIP is reached about at the end of Ti).

Such mistake shows that it is conceptually erroneous to consider the I/E ratio as a basic parameter for ventilation; indeed, it is exclusively a datum that stems from the waveform type employed for realizing an optimal oxygenation (MIP) and from the time Te needed for obtaining a value of FR which is adequate for the elimination of $CO_2$.

Figure 13:
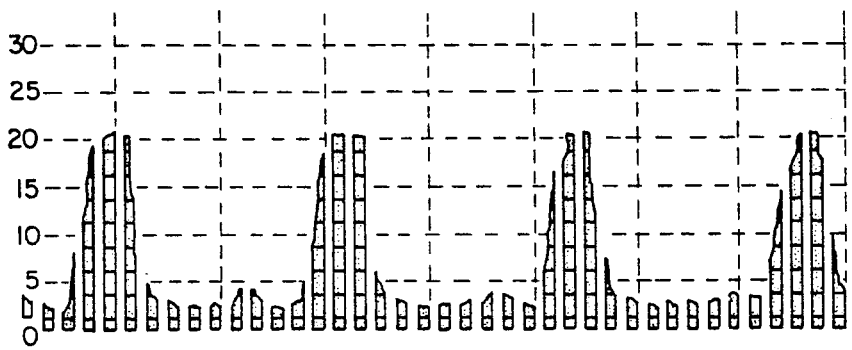
FIG. 13 shows the real time print out of the parameters of the pulmotor of the invention and of the pressure waveform detected in the ventilation circuit with the value of Ti and the shape of the waveform corrected from that shown in FIG. 12.

Such mistake has been corrected in the following (FIG. 13).

Indeed, FIG. 13 shows that the FR is equal to the preceding value, but the duration of Ti and of Te (and therefor the ratio I/E) has been much changed; moreover, a comparison of the waveform with that of FIG. 11 shows that a decrease has been obtained both of the MIP and of the MAP, the first one through the reduction of Ti and of PIP, the second one above all through the increase in the Te and the reduction in PEEP.

Finally, it is possible to observe during time Te the occurrence of small pressure oscillations which are due to the recovery of the patient's spontaneous breathing.

Figure 14:
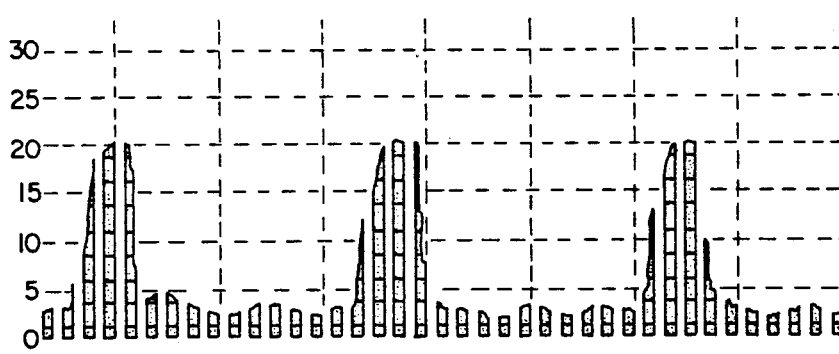
FIG. 14 shows the real time print out of the parameters of the pulmotor of the invention and of the pressure waveform detected in the ventilation circuit with the value of FR decreased from that of FIG. 13.
Figure 15:
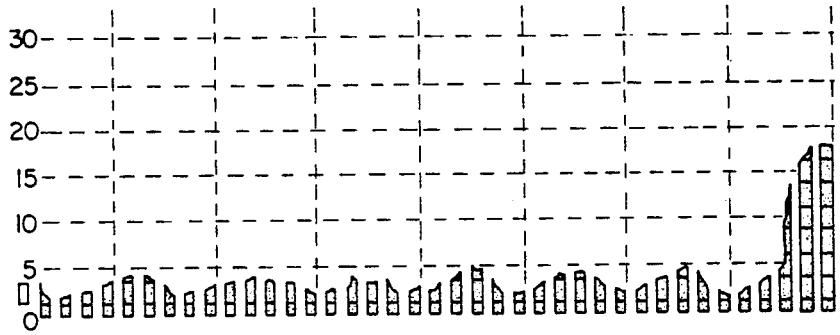
FIG. 15, shows the real time print out of the parameters of the pulmotor and of the pressure waveform detected in the ventilation circuit with the value of FR further decreased from that shown in FIG. 14.
Figure 16:
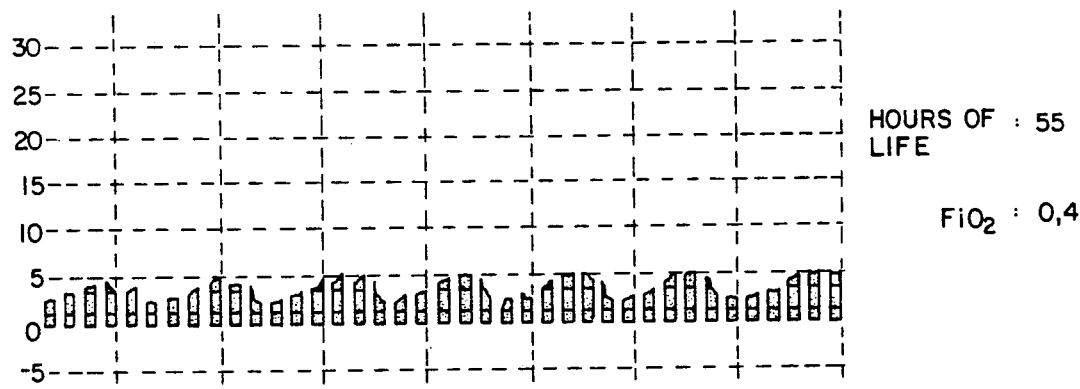
FIG. 16 shows the real time print out of the parameters of the pulmotor of the invention and of the pressure waveform detected in the ventilation circuit with the patient placed in a single continuous flow.

FIGS. 14 and 15 show that the value of FR is further decreased under control of the $PaO_2$, as the spontaneous breathing acts become more and more valid and regular.

It is to be emphasized that in the waveforms linked to the spontaneous activity of the patient, the value of the CPAP is to be read at the top of the pressure wave, to the contrary of what occurs during the IPPV; in the latter instance indeed the breathing dynamics in inverted.

The patient has been finally placed in a single continuous flow (FIG. 16) and then disintubated and placed in CPAP+3 $cmH_2O$ with a cannula through the nostril.

The present invention has been disclosed with particular reference to some specific embodiments of the same but it is to be understood that modifications and changes can be introduced in the same without departing from the spirit and scope of the invention for which a priority right is claimed.

We claim:

1. A constant flow and controlled-ventilation pulmotor for use with a patient having a respiratory circuit having an instantaneous pressure, the pulmotor being responsive to the instantaneous pressure in the respiratory circuit of the patient, the pulmotor comprising:

mixing means for proportioning amounts of air and oxygen in a desired ratio for an air and oxygen mixture, the mixture having a flow rate;

regulation means for receiving the air and oxygen mixture from said mixing means and regulating the flow rate of the mixture;

a ventilation conduit having first and second ends, said first end thereof being connected with said regulation means for supplying the air and oxygen mixture to said ventilation conduit;

a connector connected to said second end of said ventilation conduit;

a maximum pressure-responsive valve responsive to first pressure, time, and flow rate parameters, said maximum pressure-responsive valve being arranged on said ventilation conduit;

a minimum pressure-responsive valve responsive to second pressure, time and flow rate parameters;

an expiration conduit having first and second ends, said first end thereof being connected to said connector and said second end thereof being connected with said minimum pressure-responsive valve;

a pinchcock solenoid valve responsive to third pressure, time, and flow rate parameters, said pinchcock solenoid valve being arranged on said expiration conduit;

a transducer conduit having first and second ends, said first end thereof being connected to said connector;

transducer means connected to said second end of said transducer conduit for continuously detecting in real time a value of instantaneous respiration pressure of the patient and supplying an electrical signal indicative thereof;

control board means for setting the desired air to oxygen ratio of said mixing means and for setting desired values of the first, second, and third pressure, time, and flow rate parameters to which said maximum and minimum pressure-responsive valves and said pinchcock solenoid valve are respectively responsive, said control board means being connected to said mixing means, said regulation means, said minimum and maximum pressure-responsive valves, and said pinchcock solenoid valve, and said control board means generating signals representing the desired air to oxygen ratio of said mixing means and the desired first, second, and third pressure, time and flow rate parameters to which said maximum and minimum pressure-responsive valves and said pinchcock solenoid valve are respectively responsive;

electronic processor means for processing the signals from said transducer means for visualization on a video display means as a respiration waveform and for processing the signals from said control board means for visualization on the video display means as numerals; and the video display means, for continuously visualizing in the form of respiration waveforms the signals from said transducer means and for continuously visualizing in the form of numerals the signals from said control board means, whereby a person operating said pulmotor can continuously monitor the respiration waveforms of the patient and modify as necessary the parameters set on said control board means in dependence on the respiration waveforms.

2. The pulmotor of claim 1, said control board means including:

first and second control means for controlling the proportion of oxygen in the air and oxygen mixture and for regulating the flow rate of the mixture;

third and fourth control means for setting minimum and maximum values of inhalation pressure and exhalation pressure, respectively, for regulating said minimum and maximum pressure-responsive valves and said solenoid valve;

fifth and sixth control means for setting inhalation and expiration times;

seventh and eighth control means for setting alarm values for maximum and minimum values of air pressure and oxygen pressure, respectively; and a plurality of key means for activating and deactivating the respiration waveforms and the numerals on said video display means.

* * * * *